United States Patent
Suzuki

(10) Patent No.: US 10,617,852 B2
(45) Date of Patent: Apr. 14, 2020

(54) MEDICAL ELONGATED BODY AND BALLOON CATHETER

(71) Applicant: TERUMO KABUSHIKI KAISHA, Shibuya-ku, Tokyo (JP)

(72) Inventor: Kenta Suzuki, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 210 days.

(21) Appl. No.: 15/399,943

(22) Filed: Jan. 6, 2017

(65) Prior Publication Data
US 2017/0224965 A1 Aug. 10, 2017

(30) Foreign Application Priority Data

Feb. 10, 2016 (JP) .................................. 2016-024064

(51) Int. Cl.
*A61M 25/10* (2013.01)
*A61M 25/00* (2006.01)
(Continued)

(52) U.S. Cl.
CPC ....... *A61M 25/1025* (2013.01); *A61L 29/041* (2013.01); *A61L 29/06* (2013.01);
(Continued)

(58) Field of Classification Search
CPC ............ A61M 1/0086; A61M 2202/08; A61M 5/347; A61M 5/484
See application file for complete search history.

(56) References Cited

U.S. PATENT DOCUMENTS

| 4,806,182 A | 2/1989 | Rydell et al. |
| 5,017,259 A | 5/1991 | Kohsai |

(Continued)

FOREIGN PATENT DOCUMENTS

| JP | H02-191466 A | 7/1990 |
| JP | H 07-145215 A | 6/1995 |

(Continued)

OTHER PUBLICATIONS

The extended European Search Report dated Jul. 6, 2017, by the European Patent Office in corresponding European Patent Application No. 17150058.0-1501 (9 pages).

(Continued)

*Primary Examiner* — Imani N Hayman
(74) *Attorney, Agent, or Firm* — Buchanan Ingersoll & Rooney PC

(57) ABSTRACT

A medical elongated body or a balloon catheter that include a catheter main body, a tubular body, and a distal member at a distal end of the tubular body. The distal member is more flexible than the tubular body. The distal end of the tubular body is joined to the distal member at a joint portion. The tubular body includes an outer layer and an inner layer disposed inside of the outer layer in the radial direction of the tubular body. The material of the inner layer possesses better fusing properties with respect to the distal member than the fusing properties of the outer layer material with respect to the distal member material. The inner layer is interposed between the distal member and the outer layer by extending between the distal member and the outer layer at the joint portion.

14 Claims, 8 Drawing Sheets

(51) Int. Cl.
  *A61L 29/04*  (2006.01)
  *A61L 29/06*  (2006.01)
  *A61M 25/01*  (2006.01)
  *A61M 25/09*  (2006.01)

(52) U.S. Cl.
  CPC .... *A61M 25/0069* (2013.01); *A61M 25/0097* (2013.01); *A61M 25/0108* (2013.01); *A61M 25/09* (2013.01); *A61M 25/10* (2013.01); *A61M 25/104* (2013.01); *A61M 25/1034* (2013.01); *A61M 25/001* (2013.01); *A61M 25/0045* (2013.01); *A61M 2025/0081* (2013.01); *A61M 2025/1093* (2013.01)

(56) References Cited

U.S. PATENT DOCUMENTS

| | | | | |
|---|---|---|---|---|
| 6,149,996 | A | * | 11/2000 | Helgerson ........... A61M 25/001 428/147 |
| 7,815,599 | B2 | * | 10/2010 | Griffin .............. A61M 25/0069 604/103.11 |
| 2001/0051790 | A1 | | 12/2001 | Parker |
| 2007/0135830 | A1 | | 6/2007 | Schaeffer |
| 2007/0282367 | A1 | | 12/2007 | Jeffrey et al. |

FOREIGN PATENT DOCUMENTS

| | | |
|---|---|---|
| JP | H08-317987 A | 12/1996 |
| JP | H08-317988 A | 12/1996 |
| JP | 2002-509006 A | 3/2002 |
| JP | 2015-019851 A | 2/2015 |
| WO | 99/36119 A1 | 7/1999 |
| WO | WO 2011/070844 A1 | 6/2011 |

OTHER PUBLICATIONS

Office Action (Notice of Reasons for Refusal) dated Sep. 24, 2019, by the Japanese Patent Office in corresponding Japanese Patent Application No. 2016-024064 and an English Translation of the Office Action. (8 pages).

* cited by examiner

MEDICAL ELONGATED BODY AND BALLOON CATHETER

CROSS-REFERENCES TO RELATED APPLICATIONS

This application claims priority to Japanese Application No. 2016-024064 filed on Feb. 10, 2016, the entire content of which is incorporated herein by reference.

TECHNICAL FIELD

The present invention relates to a medical elongated body and a balloon catheter.

BACKGROUND ART

A medical elongated body including a catheter main body consisting of a hollow member in which a lumen is formed or a balloon catheter or the like including an inner tube shaft in which a guide wire lumen is formed may be used when performing various medical procedures in a biological organ of a living body. In general, the medical elongated body or inner tube shaft include an elongated tube body and a distal member disposed at a distal portion of the elongated tube body. In some cases, the distal member is formed of a material which is more flexible than the tube body material in order to prevent any damage to a biological lumen such as a blood vessel.

The tube body and the distal member are preferably joined to one another by fusing (i.e., a joining process such as welding or thermal bonding) so as to secure sufficient joining strength between the tube body and the distal member. However, in some cases, fusing properties between both of the tube body and the distal member deteriorate. The quality of the joint may deteriorate based on the material properties of the elements being joined, that is, the combination of a material for forming the tube body and a material for forming the distal member. In such a case, it is difficult to obtain sufficient joining strength (i.e., an adequate joint). As a result, the scope for selecting various materials constituting the tube body and the distal member becomes narrow.

International Patent Application Publication No. 2011/070844 discloses, for example, a method for stacking a part of a tube constituting an introduction destination area (corresponding to the distal member) on an inner peripheral surface side or an outer peripheral surface side of a tube body and fusing the tube body and the tube in the stacked state. According to this method, the joining strength between the tube body and the tube is improved in a portion in which the tube body and the tube are stacked. Therefore, it is considered that it is also possible to suppress the deterioration of the joining strength caused by the combination of the formation materials.

SUMMARY OF INVENTION

It remains difficult to sufficiently compensate for the deterioration of the joining strength caused by the combination of the material for forming the tube body and the material for forming the distal member by simply improving the physical joined structure between both of the tube body and the distal member in consideration of the arrangement relationship when joining the tube body and the distal member to each other.

The medical elongated body and balloon catheter here thus improve the joining strength between the tube body and the distal member in a different respect.

The medical elongated body includes a catheter main body having a lumen, in which the catheter main body has a tube body and a distal member which is disposed on a distal side of the tube body. The distal member is made of a material which is more flexible than that the tube body material. The tube body is joined to the distal member in a joint portion. The tube body has an outer layer and an inner layer inside of the outer layer in a circumferential direction. The inner layer material has better fusing properties (i.e., material compatibility for joining) with respect to the material forming the distal member than the fusing properties of the outer layer material. The inner layer is interposed between the distal member and the outer layer in the joint portion.

The balloon catheter includes: an outer tube shaft having a lumen; an inner tube shaft disposed in the lumen of the outer tube shaft; and a balloon joined to a distal portion of the inner tube shaft and a distal portion of the outer tube shaft. The inner tube shaft has a tube body and a distal member which is disposed on a distal side of the tube body and is made of a material more flexible than the tube body material. The tube body is joined to the distal member at a joint portion. The tube body has an outer layer and an inner layer inside of the outer layer in a circumferential direction. The material forming the inner layer has better fusing properties with respect to the material forming the distal member than the outer layer material. The inner layer is interposed between the distal member and the outer layer in the joint portion.

When joining the tube body of the catheter main body and the distal member to each other in the medical elongated body described above, the inner layer of the tube body (of which fusing properties with respect to the distal member are excellent) is interposed between the outer layer and the distal member of the tube body. The tube body and the distal member are thus firmly joined to each other via the inner layer of the tube body, and therefore, the joining strength between the tube body and the distal member is improved.

When joining the tube body of the inner tube shaft and the distal member to each other in the balloon catheter described above, the inner layer of the tube body (of which fusing properties with respect to the distal member are excellent) is interposed between the outer layer and the distal member of the tube body. The tube body and the distal member are thus firmly joined to each other via the inner layer of the tube body, and therefore, the joining strength between the tube body and the distal member is improved.

DETAILED DESCRIPTION

Set forth below with reference to the accompanying drawings is a detailed description of embodiments of a medical elongated body and a balloon catheter representing examples of the inventive medical elongated body and balloon catheter disclosed here.

First Embodiment

Figure 1A:
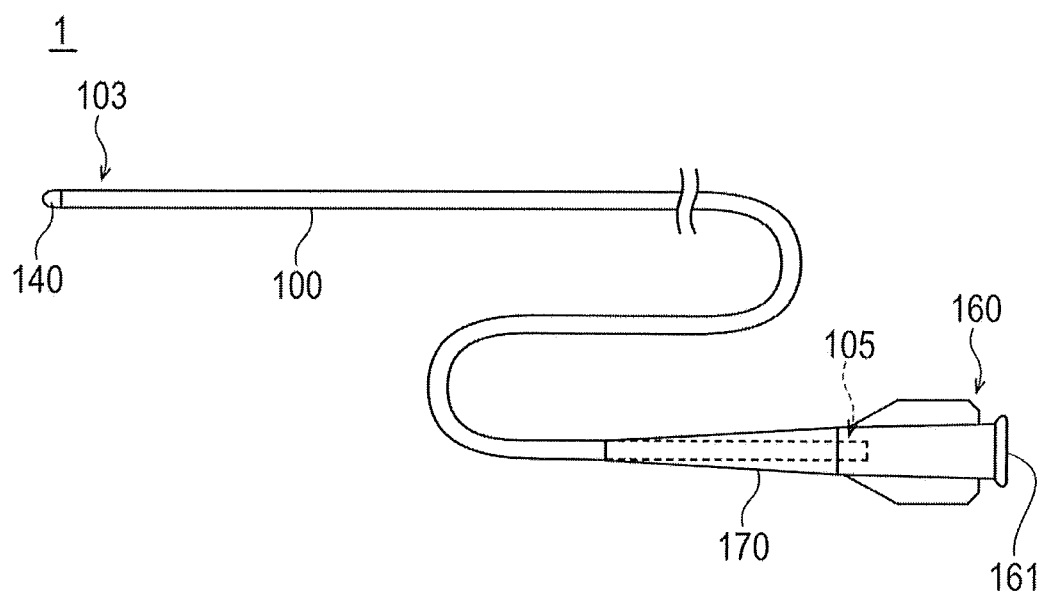
FIG. 1(A) is a view showing an overall configuration of a medical elongated body according to a first embodiment of the medical elongated body.
Figure 1B:
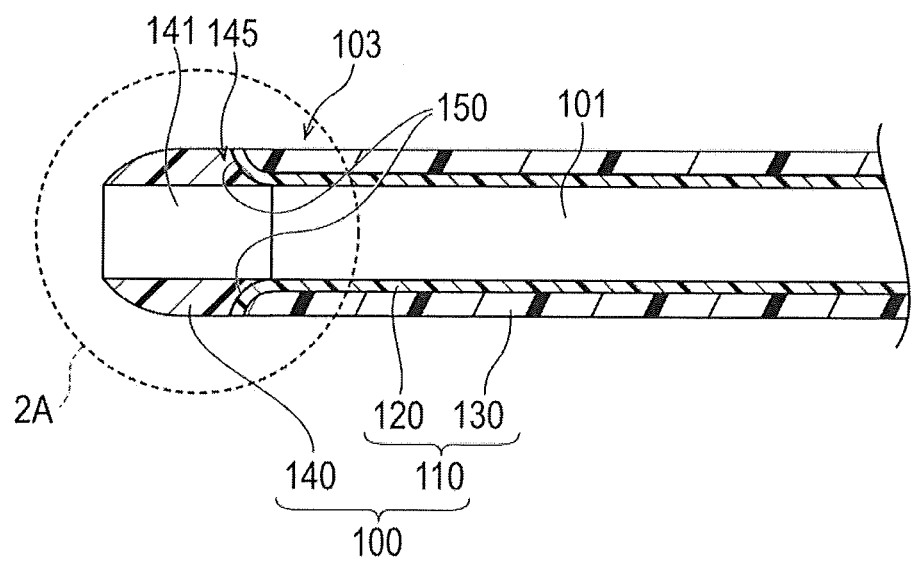
FIG. 1(B) is a cross-sectional view taken along an axial direction of a distal portion of the medical elongated body.
Figure 2:
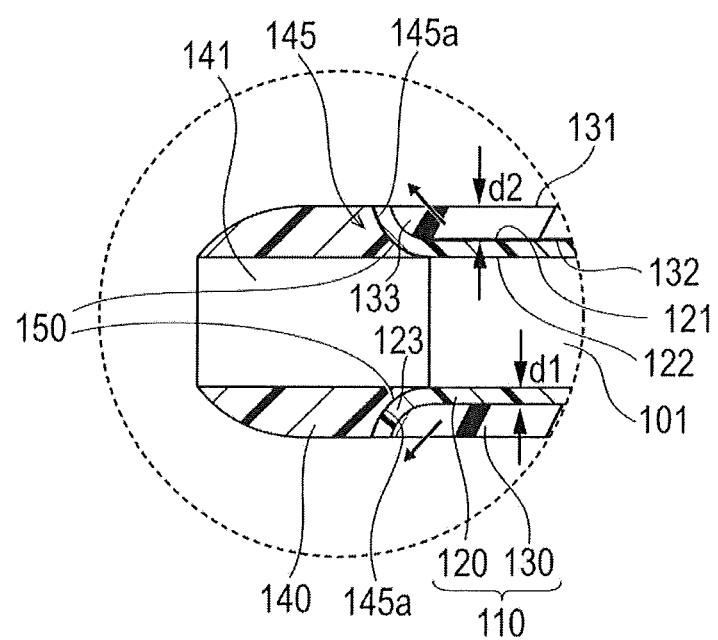
FIG. 2 is an enlarged view showing the portion identified by the broken line 2A shown in FIG. 1(B).
Figure 3:
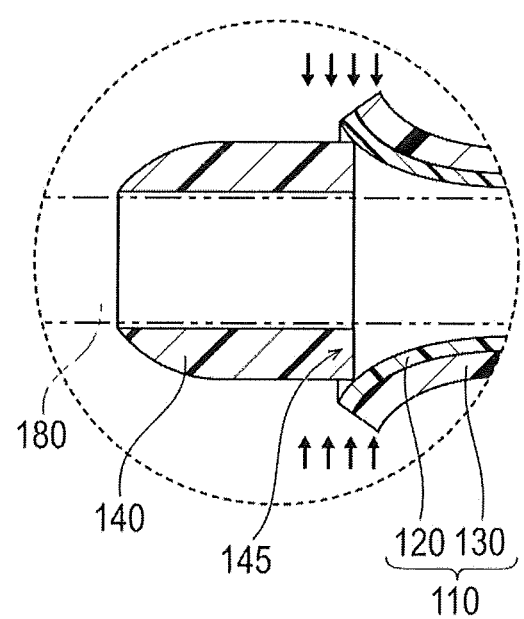
FIG. 3 is a view showing an example of a method for joining a tube body and a distal member included in the medical elongated body.

Hereinafter, a medical elongated body 1 according to a first embodiment will be described in reference to FIGS. 1(A) to 3. FIGS. 1(A), 1(B) and 2 are views showing configurations of each portion of the medical elongated body 1 and FIG. 3 is a view showing an example of a method for joining the tube body 110 and the distal member 140 of the medical elongated body 1. The dimensional ratios in each drawing may be exaggerated and/or different from the actual ratios for the convenience of description.

The medical elongated body 1 is a catheter for performing treatment, diagnosis, or the like after the medical elongated body 1 is inserted into blood vessels, bile ducts, the trachea, the esophagus, the urethra, or other biological lumens or lumens in a living body.

In the description below, the side (i.e., the left side of FIG. 1(A)) of the medical elongated body 1 that is inserted into a living body is referred to as the "distal side" or "distal end", the side of the medical elongated body 1 that has the hub 160 is referred to as the "proximal side" or "proximal end" (i.e., the right side of FIG. 1(A)), and the direction in which the catheter main body 100 (tube body 110) of the medical elongated body 1 extends is referred to as the "axial direction". A "distal portion" refers to a certain range including the distal end (i.e., the distal-most end) and the periphery thereof (i.e., a portion adjacent to the distal end, in the vicinity of the distal end), and a "proximal portion" refers to a certain range including the proximal end (i.e., the proximal-most end) and the periphery thereof (i.e., a portion adjacent to the proximal end, in the vicinity of the proximal end).

As shown in FIGS. 1(A) and 1(B), the medical elongated body 1 includes an elongated catheter main body 100 including a lumen 101.

The catheter main body 100 includes a tube body 110 extending in the axial direction and a distal member 140 disposed on the distal side of the tube body 110 as illustrated in FIG. 1(B). The distal member 140 is made of a more flexible material than the tube body 110 material.

The tube body 110 includes an outer layer 130 and an inner layer 120. A portion of the inner layer 120 is disposed on the inside of the outer layer 130 in the circumferential direction (i.e., the inner layer 120 is inside of the outer layer 130 except at the distal most end of the inner layer, as explained below). The tube body 110 and the distal member 140 are joined to each other at a predetermined joint portion 150 as shown in FIG. 2. The details of the inner layer 120, the outer layer 130, the distal member 140, and the joint portion 150 will be described below.

As shown in FIG. 1(A), the medical elongated body 1 includes a hub 160 interlocked with a proximal portion 105 of the catheter main body 100. The medical elongated body 1 also includes an anti-kink protector (strain relief) 170 disposed in the vicinity of an interlock portion of the catheter main body 100 and the hub 160 (i.e., the portion connecting the catheter main body 100 to the hub 160).

The hub 160 includes a port 161 as illustrated in FIG. 1(A). The port 161 functions as an insertion port through which a medical device (such as a guide wire) may be inserted into the lumen 101 of the catheter main body 100. The hub 160 can be attached to the outer periphery of the proximal portion 105 of the catheter main body 100. The hub 160 is attached so as to cover the outer periphery of the proximal portion of the catheter main body using, for example, an adhesive, a fixation tool (not shown in the drawing), or the like. The hub 160 material may be, for example, a thermoplastic resin such as polycarbonate, polyamide, polysulfone, and polyarylate.

The distal member 140 is formed of a material which is more flexible than the tube body 110 material (i.e., the distal member 140 material possesses greater flexibility than the tube body 110 material). The distal member 140 is also referred to as a "distal tip" of the elongated medical body. The distal member 140 is utilized to prevent any damage to a biological lumen (such as a blood vessel) and/or functions to improve insertion properties into a stenosed site formed in a blood vessel.

As shown in FIG. 2, the distal member 140 includes a portion with a tapered shape of which the outer diameter decreases toward the distal side (i.e., a portion of the distal member is tapered towards the distal end in the axial direction). A through hole 141 penetrating the distal member 140 in the axial direction is formed inside the distal member 140. The through hole 141 makes it possible to lead a medical device such as a guide wire (which has been inserted into the lumen 101 of the catheter main body 100) to the distal side of the catheter main body 100 (i.e., to protrude distally beyond the catheter main body 100 to the outer environment).

As shown in FIG. 1(B), the inner layer 120 is continuously formed along the axial direction of the tube body 110. Note that being "continuously formed" in the present specification means that the inner layer 120 extends along the inner peripheral surface of the outer layer 130 over the substantially total length of the tube body 110 in the axial direction. The tube body 110 (i.e., including the inner layer 120 material and the outer layer 130 material) may be processed/formed into a hollow tubular shape including a layered structure, through a well-known method such as coextrusion molding.

The inner layer 120 is formed of a material of which a sliding resistance is lower than that of the material forming the outer layer 130 (i.e., the inner layer 120 material possesses a lower friction coefficient than the outer layer material 130). The sliding resistance (i.e., frictional resistance) of the inner surface of the lumen (the lumen 101 of the catheter main body 100) of the tube body 110 is thus lower than the sliding resistance of the outer layer 130. Accordingly, it is possible to smoothly insert, move and remove various medical devices (such as a guide wire) into, within or from the lumen 101 of the catheter main body 100.

The inner layer 120 material possesses fusing properties with respect to the distal member 140 material that are better than the fusing properties of the outer layer 130 material. In other words, the inner layer 120 material is more compatible for being fused to (i.e., more readily joined to) the distal member 140 than the material of the outer layer 130. The inner layer 120 and the distal member 140 are fused to one another so that the tube body 110 and the distal member 140 are joined to each other via the inner layer 120 (i.e., the inner layer 120 directly contacts the distal member 140 as shown in FIG. 1(A)).

The joint portion 150 is the portion at which the tube body 110 and the distal member 140 are joined to each other. As shown in FIG. 2, the inner layer 120 of the tube body 110 is interposed between the distal member 140 and the outer layer 130 of the tube body 110 at the joint portion 150 (at least a part of the inner layer 120 extends radially outwardly between the distal member 140 and the outer layer 130 of the tube body 110 so that a part of the inner layer 120 is positioned between the distal member 140 and the outer layer 130 in the axial direction of the tube body 110). In the embodiment illustrated in FIG. 2, the joint portion 150 is formed by fusing the inner surface 122 of a distal portion 123 of the inner layer 120 to a proximal portion 145 of the distal member 140 (i.e., an outer surface of a proximal portion 145 of the distal member 140).

The inner layer 120 allows the joining force between the tube body 110 and the distal member 140 to be improved (i.e., compared to when the distal member 140 is joined to the outer layer 130). Even in a case where, for example, the outer layer 130 material possesses fusing properties with the distal member 140 that are comparatively low, it is possible to favorably keep the joining strength between the tube body 110 and the distal member 140 relatively high (i.e., a secure joint may still be formed). It is thus possible to prevent a decrease in the joining strength between the tube body 110 and the distal member 140 due to a relative joining incompatibility of the outer layer 130 material and the distal member 140 material. Therefore, the scope of materials that may be selected for the outer layer 130 and/or distal member 140 may be increased.

The inner layer 120 material, for example, may be a modified polyolefin resin. It is possible to use, for example, polymer alloy having a copolymer of olefin such as ethylene or propylene and other monomers (such as a random copolymer, a block copolymer, and a graft copolymer), or olefin as a main component, as the modified polyolefin resin. Examples of the monomer to be copolymerized include maleic anhydride, acrylic acid or a derivative thereof, methacrylic acid or a derivative thereof, vinyloxysilane, ketene acetals, dioxolane, and vinyl acetate. In addition to the above, examples of modified polyolefin resins include materials which are polyethylene such as high density polyethylene, low density polyethylene, and linear low-density polyethylene, polypropylene, an α-olefin (for example, 1-butene, 1-hexene, 4-methyl-1-pentene, 1-octene, 1-decene, or the like) polymer, an ethylene-propylene copolymer, a cycloolefin polymer (for example, a polymer of cyclic olefin such as norbornene, cyclobutene, and cyclopentene), a cycloolefin copolymer (for example, a copolymer of cyclic olefin and chain olefin such as polyethylene or a copolymer of cycloolefin and diene such as 1,4-hexadiene), and a mixture thereof and have a pendant including a polar group or a reactive group; a polyolefin resin of which the properties are changed through an acid treatment or a heat treatment; and a modified polyolefin resin which has a graft chain having alkoxyalkylacrylate disclosed in Japanese Patent Application Publication No. 07-145215 as a constituent component. In the case of the copolymers, the structures of the copolymers are not particularly limited. A random copolymer, an alternating copolymer, a periodic copolymer, a graft copolymer, and a block copolymer can be suitably used.

The outer layer 130 material, for example, may be a polyamide resin. Examples of the polyamide resin include a homopolymer such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12); and copolymers such as a caprolactam/lauryl lactam copolymer (nylon 6/12), a caprolactam/aminoundecanoic acid copolymer (nylon 6/11), a caprolactam/ω-aminononanoic acid copolymer (nylon 6/9), a caprolactam/hexamethylene diammonium adipate copolymer (nylon 6/66), a copolymer of adipic acid and metaxylenediamine, or a copolymer of hexamethylene diamine and m-, p-phthalic acid. Here, as the polyamide resin, a synthetic product may be used or a commercially available product may be used.

The distal member 140 material, for example, may be a polyurethane resin. It is preferable to use, for example, a polyurethane resin formed of diisocyanate, a chain extender, and a polyol as the polyurethane resin. Here, there is a polyether polyol, a polyester polyol, and a polycarbonate polyol in the polyol. Examples of the polyether polyol include polyethylene glycol, polypropylene glycol, polybutylene glycol, polytetramethylene glycol, polycaprolactone glycol, polyadipate glycol, and polyether glycol. Examples of the polyester polyol include a poly-ε-caprolactone polyol, a polyethylene terephthalate polyol, and a polyethylene adipate polyol. In addition, particularly in a polyurethane resin in which a polyol is a polycarbonate polyol, the polyurethane resin is hardly affected by hydrolysis or radicals and is excellent in durability. It is thus possible to suitably use the polyurethane resin for indwelling in a living body for a long period of time. Examples of the polycarbonate polyol include a polyhexamethylene carbonate polyol, a polypentamethylene carbonate polyol, a polytetramethylene carbonate polyol, a polytrimethylene carbonate polyol, a polydecamethylene carbonate polyol, a polydiethylene carbonate polyol, and a poly-p-xylylene carbonate polyol. In addition, examples of the diisocyanate include diphenylmethane-4,4'-diisocyanate, naphthalene diisocyanate, tolylene diisocyanate, tetramethyl xylene diisocyanate, xylene diisocyanate, dicyclohexane diisocyanate, dicyclohexylmethane diisocyanate, hexamethylene diisocyanate, and isophorone diisocyanate. Examples of the chain extender include 1,4-butanediol, 1,6-hexanediol, ethylene glycol, diethylene glycol, triethylene glycol, propylene glycol, glycerin, trimethylolpropane, pentaerythritol, sorbitol, and methylene glycoside. Alternately, urea bonding may be partially introduced using ethylenediamine, buthylenediamine, hexamethylenediamine, or the like as the chain extender.

In general, the polyurethane resin has flexibility (i.e., is flexible) and possesses a higher impact resilience than the flexibility and impact resilience of the polyamide resin. Based on this configuration, the medical elongated body 1 can suitably suppress damage to a biological lumen such as a blood vessel by forming the distal member 140 out of a polyurethane resin. Forming the distal member 140 out of a polyurethane resin can also improve followability to a guide wire which has been inserted into the tube body 110. The distal member 140 thus can suitably improve insertion properties into a stenosed site formed in a blood vessel or the like.

The fusing properties between the polyurethane resin and the modified polyolefin resin are high (i.e., these materials are highly compatible for fusing) compared to the fusing properties between the polyurethane resin and the polyamide resin. Accordingly, it is possible to increase the joining force between the distal member 140 and the tube body 110 by forming the inner layer 120 using a modified polyolefin resin and the distal member 140 using a polyurethane resin even when the outer layer 130 material is a polyamide resin.

As shown in FIG. 2, the distal member 140 is fused to the inner layer 120 with the end surface 145a of the proximal portion 145 of the distal member 140 directly abutting/contacting the distal portion 123 of the inner layer 120 of the tube body 110. Fusing the distal member 140 to the inner layer 120 is performed by heating and pressing the distal member 140 and the inner layer 120 toward the radially inside from the outer periphery of the tube body 110 as illustrated in FIG. 3. The fusing is performed with the inner layer 120 of the tube body 110 disposed to cover the outer surface of the proximal portion 145 of the distal member 140.

The inner layer 120 of the tube body 110 has an outer surface 121 disposed on the outer layer 130 side (i.e., opposite to/abutting the inner surface of the outer layer 130). The inner layer 120 has an inner surface 122 disposed on the lumen 101 side. Similarly, the outer layer 130 of the tube body 110 has an outer surface 131 and an inner surface 132 which is disposed on the inner layer 120 side.

As shown by the arrows of FIG. 2, the inner surface 132 of the outer layer 130 is inclined toward the outer surface 131 of the outer layer 130 at a distal portion 133 of the outer layer 130. The outer surface 121 and the inner surface 122 of the inner layer 120 are inclined toward the outside (outside in a radial direction of the tube body 110). The outer surface 121 of the inner layer 120 extends in contact with and along the inner surface 132 of the outer layer 130 at the distal portion 123 of the inner layer 120. The inner layer 120 at the joint portion 150 (a portion of the inner layer 120 that forms the joint portion 150) is disposed between the outer layer 130 and the distal member 140 in the axial direction of the tube body 110. The cross section view illustrated in FIG. 2 shows the inner layer 120 positioned between the outer layer 130 and the distal member 140 in the axial direction of the tube body 110.

The inner layer 120 at the joint portion 150 is sandwiched between the outer layer 130 and the distal member 140 in the cross section taken along the axial direction of the tube body 110. Note that being "sandwiched" as used in the present specification means that the inner layer 120 is interposed (intervened) between the distal member 140 and the outer layer 130 without any space along a thickness direction (vertical direction in FIG. 2) between the end surface 145a of the proximal portion 145 of the distal member 140 and the inner surface 122 of the inner layer 120 as shown in FIG. 2.

As shown in FIG. 2, the wall thickness d1 of the inner layer 120 is smaller (i.e., the inner layer 120 wall is thinner) than the wall thickness d2 of the outer layer 130 proximal to the joint portion 150 in the cross section taken along the axial direction of the tube body 110.

For example, even when the wall of the inner layer 120 is formed to be thinner than the wall of the outer layer 130 (i.e., the wall thickness d1 of the inner layer 120 is less than the wall thickness d2 of the outer layer 130) in a stage of manufacturing the tube body 110, there is a possibility that the wall thickness of the inner layer 120 becomes larger than that of the outer layer 130 in the joint portion 150 depending on heat, pressure, or the like applied to the vicinity of the joint portion 150 when fusing the inner layer 120 to the distal member 140. For this reason, a site where the wall thickness is not significantly changed before and after formation of the joint portion 150 (that is, a site proximal to the joint portion 150) is selected as the site where the wall thickness d1 of the inner layer 120 and the wall thickness d2 of the outer layer 130 are compared to each other.

Next, an example of a method for joining the tube body 110 and the distal member 140 will be described in reference to FIG. 3.

The tube body 110, for example, may include a distal portion which has been subjected to flaring processing so as to be widened to the outside (i.e., possess a larger outer diameter at the distal portion than the outer diameter of the tube body 110 proximal to the distal portion).

When joining the tube body 110 and the distal member 140 to one another, the distal portion of the tube body 110 (which has been subjected to flaring processing) is disposed to cover (i.e., overlap in the axial direction) the outer surface of the proximal portion 145 of the distal member 140 as shown in FIG. 3. A heat shrinkable tube (not shown in the drawing) is disposed on the outer periphery of the tube body 110 while a core bar 180 is inserted into the lumen (through hole 141) of the distal member 140 and the lumen of the tube body 110. The inner layer 120 of the tube body 110 is fused to the distal member 140 by applying heat from the outer peripheral side of the heat shrinkable tube. The portion of the inner layer 120 which has been fused forms the joint portion 150 at which the distal member 140 and the inner layer 120 are joined to each other.

By using the operation described above, the distal portion 123 of the inner layer 120 can form, for example, a shape which is curved and inclined towards the radially outside of the medical elongated body 1 in the cross section taken along the axial direction of the distal portion of the medical elongated body 1 as illustrated in FIG. 2. The inner surface 132 of the distal portion 133 of the outer layer 130 can form a shape which is curved and inclined towards the outer surface 131 side of the outer layer 130 along the distal portion 123 of the inner layer 120.

Note that the sectional shape of the distal member 140 before being joined to the tube body 110 is not limited to the shape exemplified in FIG. 3. For example, a concave step portion or the like may be formed in the proximal portion 145 of the distal member 140 so that the distal portion of the tube body 110 (which has been subjected to flaring processing) can be positioned in the concave step portion or the like.

The medical elongated body 1 according to the present embodiment includes the catheter main body 100 having the lumen 101 as described above. The catheter main body 100 has the tube body 110 and the distal member 140 positioned distal to the tube body 110. The distal member 140 is made of a more flexible material than the tube body 110. The tube body 110 is joined to the distal member 140 at the joint portion 150. The tube body 110 has the outer layer 130 and the inner layer 120 which is disposed inside of the outer layer 130 in the circumferential direction. The material forming the inner layer 120 has better fusing properties with respect to the distal member 140 material than the fusing properties of the material forming the outer layer 130. The inner layer 120 is interposed between the distal member 140 and the outer layer 130 at the joint portion 150.

In the medical elongated body 1 described above, the inner layer 120 of the tube body 110 (which has better fusing properties with respect to the distal member 140) is interposed between the distal member 140 and the outer layer 130 of the tube body 110 when the distal member 140 and the tube body 110 are joined to each other. Since the tube body 110 is firmly joined to the inner layer 120 of the tube body 110, the joining strength between the tube body and the distal member is improved because the inner layer 120 material has better fusing properties (i.e., fusing compatibility) with respect to the distal member 140 than the outer layer 130 material.

The outer layer 130 has an outer surface 131 and an inner surface 132 which is disposed on the inner layer 120 side. The inner surface 132 of the outer layer 130 is inclined toward the outer surface 131 of the outer layer 130 at the distal portion 133 of the outer layer 130 (i.e., the inner surface 132 diameter of the distal portion 133 increases in the axial direction towards the distal-most end of the distal portion 133). The inner layer 120 at the joint portion 150 is disposed between the outer layer 130 and the distal member 140 in the cross section taken along the axial direction of the tube body 110. Since the medical elongated body is configured in this manner, the inner layer 120 is joined to the distal member 140 while being inclined at the same inclination as the inner surface 132 of the outer layer 130 (i.e., the inner layer 120 is in contact with and extends along the inner surface 132 of the outer layer 130). Accordingly, it is possible to make the contact area (joint area) between the inner layer 120 and the distal member 140 relatively large, and therefore, it is possible to further improve the joining strength between the tube body 110 and the distal member 140.

The inner layer 120 in the joint portion 150 is sandwiched between the outer layer 130 and the distal member 140 in the cross section taken along the axial direction of the tube body 110. Since the medical elongated body is configured in this manner, it is possible to increase the size of the portion of the inner layer 120 interposed between the outer layer 130 and the distal member 140. Therefore, it is possible to further improve the joining strength between the tube body 110 and the distal member 140.

The inner layer 120 is extends continuously along the axial direction of the tube body 110. The inner layer 120 material possesses a lower sliding resistance (i.e., a lower friction coefficient) than the outer layer 130 material. Since the inner layer 120 is continuously formed along the axial direction of the tube body 110, the inner layer 120 and the outer layer 130 are firmly integrated. Therefore, it is possible to prevent the inner layer 120 and the outer layer 130 from being separated from each other. It is thus possible to more firmly join the tube body 110 and the distal member 140 to each other. The sliding resistance of the inner layer 120 is lower than that of the outer layer 130, so that the sliding properties (i.e., slidability or maneuverability) of the medical device (such as a guide wire) to be inserted into the tube body 110 are improved.

The wall thickness d1 of the inner layer 120 is smaller (i.e., the wall is thinner) than the wall thickness d2 of the outer layer 130 (in the cross section taken along the axial direction of the tube body 110) proximal to the joint portion 150. For this reason, it is possible to use a relatively lower amount of material to form the inner layer 120 playing a role as a joining member which joins the distal member 140 and the outer layer 130 to each other.

Modification Example

Figure 4:
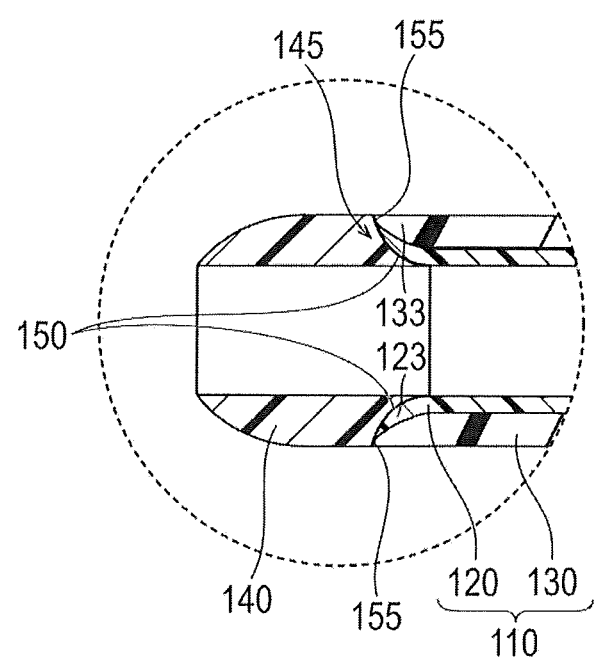
FIG. 4 is a cross-sectional view of a distal portion of a medical elongated body according to a modification example of the first embodiment.

A medical elongated body 1 according to a modification example of the first embodiment is shown in FIG. 4.

In the embodiment illustrated in FIGS. 1(A)-2 described above, the inner layer 120 in the joint portion 150 is sandwiched between the outer layer 130 and the distal member 140 in the cross section taken along the axial direction of the tube body 110. In contrast, FIG. 4 illustrates a modification example with a non-intervention portion 155. The non-intervention portion 155 includes a portion in which the inner layer 120 is not interposed between the outer layer 130 and the distal member 140. Even when this non-intervention portion 155 is formed, it is possible to fuse the inner layer 120 directly to the distal member 140 if at least a part of the inner layer 120 is interposed between the outer layer 130 and the distal member 140. Accordingly, it remains possible to improve the joining strength between a tube body 110 and the distal member 140 even in the medical elongated body 1 shown in the modification example where only a portion of the inner layer 120 is positioned between the outer layer 130 and the distal member 140.

When the non-intervention portion 155 is formed as described in this modification example, the sectional shape of a distal portion 123 of the inner layer 120 can be formed in, for example, an arc-shaped sectional shape which is tapered and curved toward the non-intervention portion 155 side as shown in FIG. 4.

Second Embodiment

Next, a balloon catheter 2 embodiment as illustrated in FIGS. 5(A)-6(B) will be described. FIGS. 5(A)-6(B) are views illustrating the configurations of different portions of the balloon catheter 2.

The balloon catheter 2 is a medical device which treats a stenosed site (lesion area) by widening the stenosed site. The balloon catheter 2 widens the stenosed site by inserting an elongated shaft 200 into a biological organ and dilating a balloon 20 disposed on a distal side of the shaft 200 within the stenosed site.

Figure 5A:
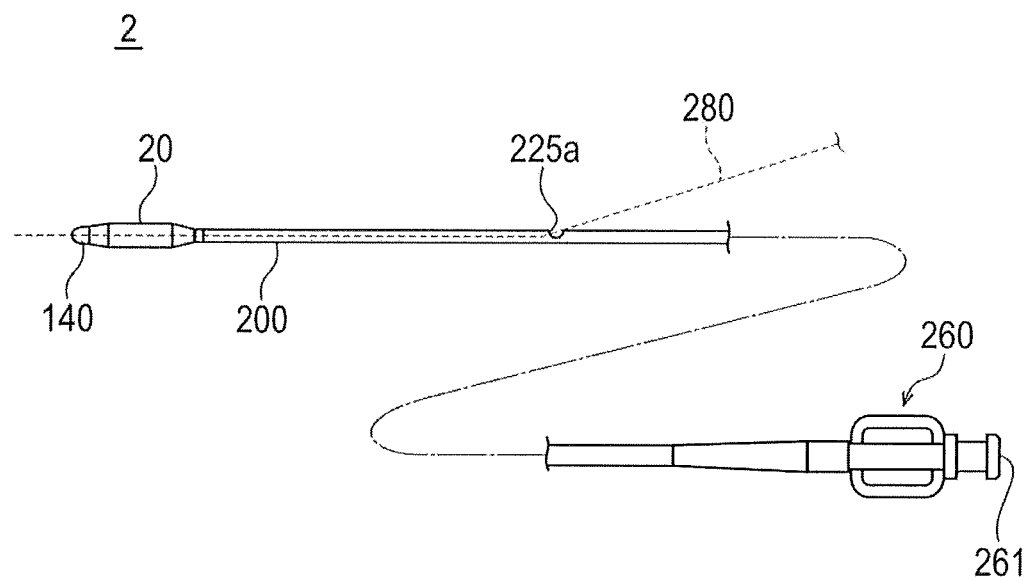
FIG. 5(A) is a view showing an overall configuration of a balloon catheter according to another embodiment and FIG. 5(B) is a cross-sectional view taken along an axial direction of a distal portion of the balloon catheter.

The balloon catheter 2 illustrated in FIG. 5(A) is a balloon catheter for PTCA (percutaneous transluminal coronary angioplasty) expansion which is used for widening a stenosed site of the coronary artery. It is possible to, for example, use the balloon catheter 2 to treat and improve a stenosed site formed in other blood vessels, bile ducts, the trachea, the esophagus, other digestive tracts, the urethra, the lumen of the nose and ears, and other biological organs such as organs. The balloon catheter 2 may also be a balloon catheter for delivering a medical instrument (such as a stent) within a living body.

In the below description regarding the balloon catheter 2 embodiment illustrated in FIG. 5(A), the side (a left side of FIG. 5(A)) on which the balloon catheter 2 is inserted into a living body is referred to as the "distal side" or "distal end", the side on which a hub 260 is disposed in the balloon catheter 2 is referred to as the "proximal side" or the "proximal end", and the direction in which the shaft 200 (tube body 110) of the balloon catheter 2 extends is referred to as the "axial direction". A "distal portion" refers to a certain range including a distal end (i.e., the distal-most end) and the periphery thereof (i.e., a portion in the vicinity of the distal end), and a "proximal portion" refers to a certain range including a proximal end (i.e., the proximal-most end) and the periphery thereof (i.e., a portion in the vicinity of the proximal end).

As shown in FIG. 5, the balloon catheter 2 includes an outer tube shaft 210 having a lumen 211, an inner tube shaft 220 disposed in the lumen 211 of the outer tube shaft 210, and a balloon 20 joined to the outer surface of the distal portion 223 of the inner tube shaft 220 and the outer surface of the distal portion 213 of the outer tube shaft 210.

The outer tube shaft 210 and the inner tube shaft 220 constitute the shaft 200. The shaft 200 is formed of a double-tube structure in which the inner tube shaft 220 and the outer tube shaft 210 are disposed by being concentrically positioned. The inner tube shaft 220 is interpolated into (i.e., extends within) the outer tube shaft 210. The balloon catheter 2 illustrated in FIG. 5(A) is a so-called rapid exchange type which includes a proximal deformation portion (a proximal deformation portion of the inner tube shaft 220) 225a. A guide wire 280 is insertable through the proximal deformation portion 225a and through to the distal portion side of the shaft 200. Note that the inner tube shaft 220 and the outer tube shaft 210 may be non-concentrically positioned.

Figure 5B:
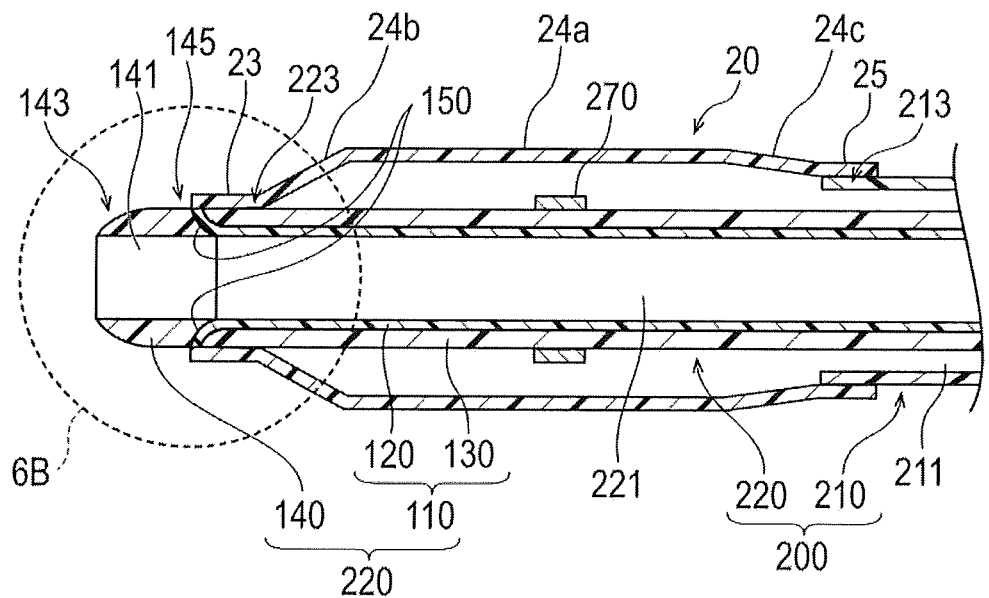
Figure 6A:
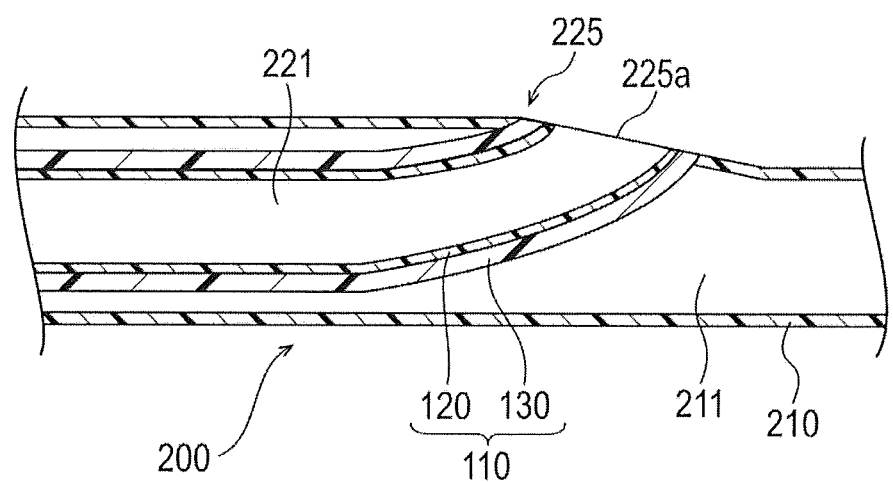
FIG. 6(A) is a cross-sectional view of the vicinity of a proximal deformation portion of an inner tube shaft included in a balloon catheter.

As shown in FIGS. 5(B) and 6(A), the inner tube shaft 220 has a tubular shape and includes a guide wire lumen 221. The guide wire 280 is insertable into the guide wire lumen 221. The proximal portion 225 of the inner tube shaft 220 has a curved shape such that the proximal deformation portion 225a faces radially outside of the balloon catheter 2.

The lumen 211 provided in the outer tube shaft 210 is a pressurizing medium lumen to circulate a pressurizing medium between the lumen 211 and the inner tube shaft 220.

As shown in FIG. 5(A), the hub 260 is disposed at the proximal portion of the shaft 200. The hub 260 includes a port 261 which can be liquid-tightly and air-tightly connected to a supply device (not shown in the drawing) such as an indeflator for supplying a pressurizing medium to the balloon 20. The port 261 of the hub 260 can be formed by, for example, well-known Luer Taper or the like which is configured such that a fluid tube or the like can be connected to the port 261 and separated from the port 261. The pressurizing medium (for example, physiological salt solution or contrast agent) can be made to flow into the lumen 211 of the outer tube shaft 210 through the port 261 of the hub 260. The pressurizing medium is supplied to (injected into) the balloon 20 via the lumen 211.

Figure 6B:
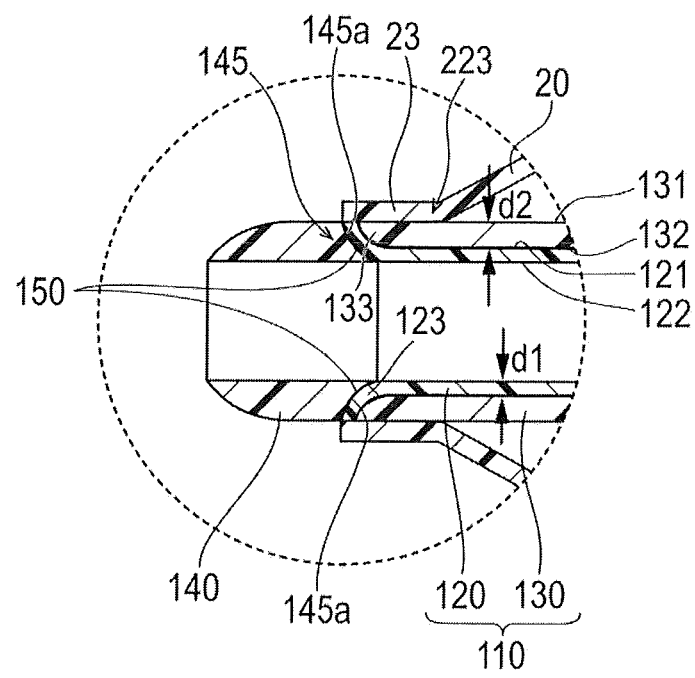
FIG. 6(B) is an enlarged view showing the portion identified by the broken line 6B shown in FIG. 5(B).

The inner tube shaft 220 includes the tube body 110 and a distal member 140 which is disposed on a distal side of the tube body 110 as illustrated in FIGS. 5(B) and 6(B). The configurations of the tube body 110, the distal member 140, and the joint portion 150 which joins the tube body 110 to the distal member 140 are substantially the same as those described in the first embodiment.

As shown in FIG. 6(B), an inner layer 120 of the tube body 110 is interposed (positioned) between the distal member 140 and an outer layer 130 at the joint portion 150. An inner surface 122 of a distal portion 123 of the inner layer 120 constituting the joint portion 150 is fused to the distal member 140. The tube body 110 and the distal member 140 are thus joined to each other at the joint portion 150.

Similarly to the medical elongated body described above, an inner surface 132 of the outer layer 130 is inclined toward an outer surface 131 of the outer layer 130 at a distal portion 133 of the outer layer 130. The inner layer 120 at the joint portion 150 is sandwiched between the outer layer 130 and the distal member 140. The inner layer 120 extends continuously along the axial direction of the tube body 110 (e.g., a portion of the inner layer 120 is an elongated portion that continuously extends in the axial direction in contact with the outer layer 130). The inner layer 120 material possesses a sliding resistance that is lower than that the sliding resistance of outer layer 130 material.

Similarly to the description above regarding the embodiment illustrated in FIG. 1(A), the wall thickness d1 of the inner layer 120 is less than the wall thickness d2 of the outer layer 130 proximal to the joint portion 150 in the cross section taken along the axial direction of the tube body 110. In other words, the inner layer 120 wall is thinner than the outer layer 130. As will be described below, favorable fusing properties can be obtained by using a polyamide resin as the material for the balloon 20, the outer layer 130, and the outer tube shaft 210. For this reason, an outer layer 130 made of a polyamide resin with a relatively large wall thickness d2 (i.e., the outer layer 130 has a relatively thick wall) can be suitably joined to a balloon 20 and an outer tube shaft 210 that are made of a polyamide resin.

As shown in FIG. 5(B), an X-ray imaging marker 270 indicating the center of the balloon 20 in the axial direction is provided in the tube body 110 of the inner tube shaft 220. The X-ray imaging marker 270, for example, may be a fine metal wire which has a small diameter and is made of a radiopaque material. Examples of radiopaque materials include metals such as platinum, gold, silver, titanium, and tungsten, or alloys of these metals. A resin material containing powder of a radiopaque material may also be used for the X-ray imaging marker 270.

The balloon 20 illustrated in FIG. 5(B) includes a straight-shaped (i.e., cylindrically shaped) dilation valid portion (pressurization portion) 24a which widens a stenosed site formed in a biological lumen (such as a blood vessel) by dilating and deforming. The dilation valid portion 24a is connected to tapered portions 24b and 24c respectively provided on the distal side and the proximal side of the dilation valid portion 24a.

A distal portion 23 of the balloon 20 is joined to the inner layer 120 and the outer layer 130 of the tube body 110 as shown in FIG. 5(B). A proximal portion 25 of the balloon 20 is joined to the distal portion 213 of the outer tube shaft 210 (i.e., the outer surface of the distal portion 213 of the outer tube shaft 210).

As shown in FIG. 6(B), the distal portion 23 of the balloon 20 is joined to the tube body 110 to cover a portion exposed on the outer surface from a space between the distal member 140 and the outer layer 130 in the inner layer 120, and the outer surface 131 of the distal portion 133 of the outer layer 130. The joining is performed through fusing with respect to the inner layer 120 and fusing with respect to the outer layer 130. In other words, the distal portion 23 of the balloon is joined to both an outer surface of the distal-most end of the inner layer 120 and an outer surface of the distal-most end of the outer layer 130.

The tube body 110 and the distal member 140 can be joined to each other as described above in the first embodiment (e.g., as illustrated in FIG. 3). The balloon 20 can be joined to the shaft 200, for example, by fusing the distal portion 23 to the distal portion 223 of the inner tube shaft 220 after joining the tube body 110 to the distal member 140, and by fusing the proximal portion 25 to the distal portion 213 of the outer tube shaft 210.

Similarly to the first embodiment, it is possible to use, for example, a modified polyolefin resin as the material forming the inner layer 120 of the tube body 110. In addition, similarly to the first embodiment, it is possible to use, for example, a polyamide resin as the material forming the outer layer 130 of the tube body 110. It is also possible to use, for example, a polyurethane resin as the material forming the distal member 140, as explained above in regards to the embodiment illustrated in FIG. 1(A).

The balloon 20 and the outer tube shaft 210, for example, may be formed out of a polyamide resin.

It is possible to use, for example, materials exemplified in the first embodiment as each of the modified polyolefin resin, the polyamide resin, and the polyurethane resin.

Favorable fusing/joining properties are created when the inner layer 120 is a modified polyolefin resin and the distal member 140 is a polyurethane resin. This combination of materials makes it possible to improve the joining strength between the tube body 110 and the distal member 140.

Favorable fusing/joining properties can also be induced when the balloon 20, the outer layer 130, and the outer tube shaft 210 are formed of a polyamide resin. This configuration of materials makes it possible to improve the joining strength between the balloon 20 and the outer layer 130 (inner tube shaft 220) and the joining strength between the balloon 20 and the outer tube shaft 210.

The balloon catheter 2 according to the present embodiment as described above has the outer tube shaft 210 having the lumen 211; the inner tube shaft 220 disposed in the lumen 211 of the outer tube shaft 210; and the balloon 20 joined to the distal portion 223 of the inner tube shaft 220 and the distal portion 213 of the outer tube shaft 210. The inner tube shaft 220 has the tube body 110 and the distal member 140 which is disposed on the distal side of tube body 110 and is made of a material which is more flexible than that of the tube body 110. The tube body 110 is joined to the distal member 140 at the joint portion 150. The tube body 110 has the outer layer 130 and the inner layer 120 disposed on the inside of the outer layer 130 in the circumferential direction. The inner layer 120 is made of a material with a sliding resistance that is lower than that the sliding resistance of the material forming the outer layer 130. The material forming the inner layer 120 has better fusing properties with respect to the material forming the distal member 140 than the material forming the outer layer 130. The inner layer 120 is interposed between the distal member 140 and the outer layer 130 at the joint portion 150 so that it extends radially outwardly between the outer layer 130 and the distal member 140 at the joint portion 150.

In the balloon catheter 2 constituted as described above, the inner layer 120 of the tube body 110 (which has better fusing properties with respect to the distal member 140) is interposed between the distal member 140 and the outer layer 130 of the tube body 110 when joining the distal member 140 and the tube body 110 of the inner tube shaft 220 to each other. The tube body 110 and the distal member 140 are firmly joined to each other through the inner layer 120 of the tube body 110, and therefore, the joining strength between the tube body 110 and the distal member 140 is improved. Furthermore, the sliding resistance of the inner layer 120 of the tube body 110 is lower than that of the outer layer 130 of the tube body 110. It is thus possible to improve the sliding properties (i.e., slidability or maneuverability) of a medical device such as a guide wire to be inserted into the tube body 110.

The inner layer 120 of the tube body 110 is made of a modified polyolefin resin and the distal member 140 is made of a polyurethane resin. Using a polyurethane resin for the distal member 140 makes it is possible to suitably suppress any damage to a biological lumen (such as a blood vessel) while also improving the joining strength between the tube body 110 and the distal member 140. This material also makes it possible to suitably improve insertion properties into a stenosed site formed in a blood vessel or the like.

The outer layer 130 of the tube body 110, the outer tube shaft 210, and the balloon 20 each are made of a polyamide resin. It is possible to provide predetermined compliance suitable for widening a stenosed site (which is formed in a biological lumen such as a blood vessel) while improving the joining strength between the balloon 20 and the outer layer 130 and the joining strength between the balloon 20 and the outer tube shaft 210 by forming the balloon 20 using a polyamide resin.

In addition, the inner layer 120 is continuously formed along the axial direction of the tube body 110. The inner layer 120 material has a sliding resistance lower than of the sliding resistance of the material forming the outer layer 130. Since the inner layer 120 is continuously formed along the axial direction of the tube body 110, the inner layer 120 and the outer layer 130 are firmly integrated (i.e., affixed/connected to one another). Therefore, it is possible to prevent the inner layer 120 and the outer layer 130 from being separated from each other. Accordingly, it is possible to more firmly join the tube body 110 and the distal member 140 to each other. The sliding resistance of the inner layer 120 is lower than that of the outer layer 130 to make it possible to improve the sliding properties of a medical device such as a guide wire that may be inserted into the tube body 110.

Modification Example 1

Figure 7:
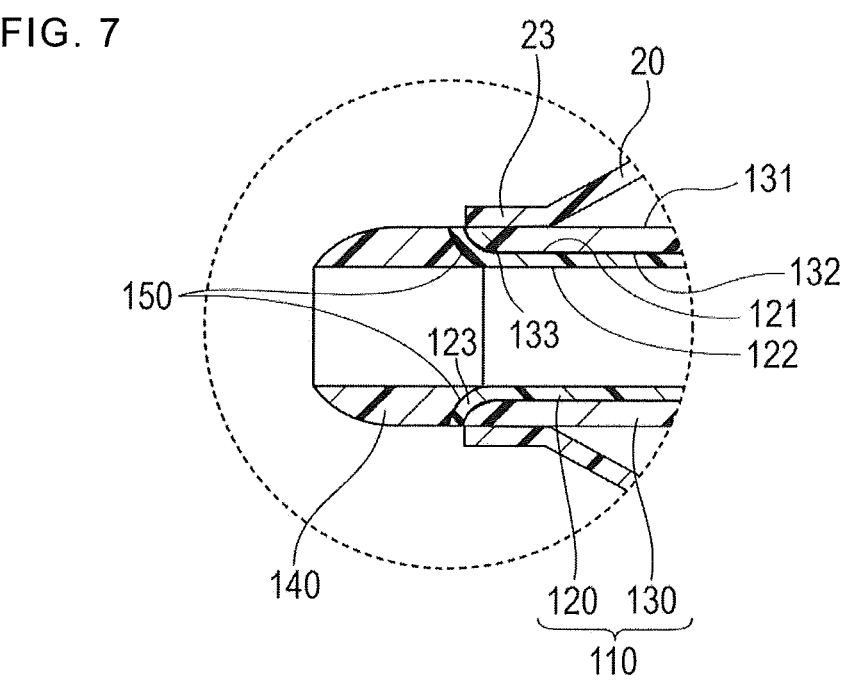
FIG. 7 is a cross-sectional view of a distal portion of a balloon catheter according to a modification example of the balloon catheter illustrated in FIG. 5(A).

A balloon catheter 2 according to a modification example 1 of the second embodiment is shown in FIG. 7.

In the embodiment illustrated in FIGS. 5(A)-6(B) and described above, the distal portion 23 of the balloon 20 is joined to both an outer surface of the inner layer 120 and an outer surface of the outer layer 130 of the tube body 110. In contrast, in the modification example 1 shown in FIG. 7, the distal portion 23 of the balloon 20 is joined to only the outer surface of the outer layer 130 of the tube body 110. The distal portion 23 of the balloon 20 may be joined to both the inner layer 120 and the outer layer 130, to only the outer layer 130, only the inner layer 120, or the like.

Modification Example 2

Figure 8:
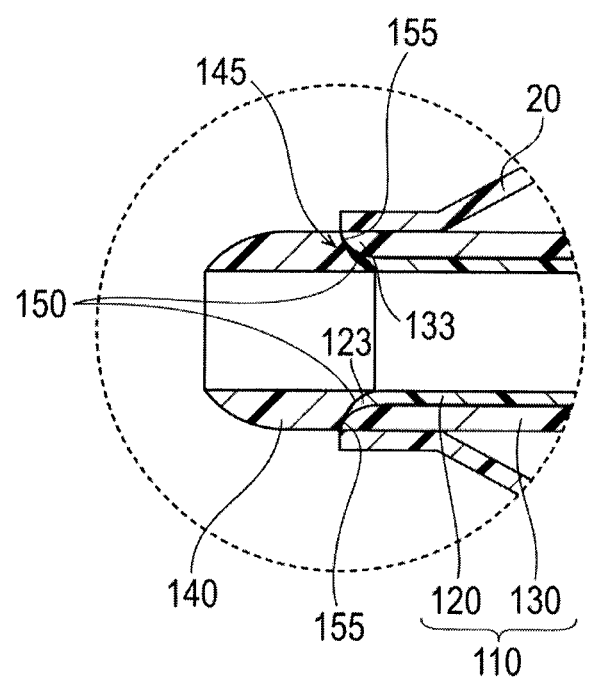
FIG. 8 is a cross-sectional view of a distal portion of a balloon catheter according to a second modification example of the balloon catheter illustrated in FIG. 5(A).

A balloon catheter 2 according to a modification example 2 of the second embodiment is shown in FIG. 8.

In the embodiment described above and illustrated in FIGS. 5(A)-6(B), the inner layer 120 at the joint portion 150 is sandwiched between the outer layer 130 and the distal member 140 in the cross section taken along the axial direction of the tube body 110 (i.e., a portion of the inner layer 120 fully separates the outer layer 130 from the distal member 140 in the axial direction). In contrast, the modification example in FIG. 8 illustrates a non-intervention portion 155 such that the inner layer 120 is not interposed between the outer layer 130 and the distal member 140. Even in the case where such a non-intervention portion 155 is formed, it is possible to fuse the inner layer 120 with the distal member 140 if at least a part of the inner layer 120 is interposed between the outer layer 130 and the distal member 140. Fusing at least part of the inner layer 120 to the distal member 140 improves the joining strength between the tube body 110 and the distal member 140.

When the non-intervention portion 155 shown in FIG. 8 is included, there is not a portion of the inner layer 120 that is exposed to the outside environment (i.e., there is not a space between the outer layer 130 and the distal member 140). This configuration allows the balloon 20 to be joined to, for example, only the outer layer 130.

In the above description, the inventive medical elongated body and balloon catheter are described in reference to certain embodiments. However, the inventive medical elongated body and balloon catheter are not limited to only the configurations described in the embodiments, and can be appropriately changed based on the description of claims.

For example, the sectional shapes (sectional shapes taken along the axial direction) of the distal members are not limited to the shapes shown in the drawings. The sectional shape of the inner layer in a portion interposed between the distal member and the outer layer, the thickness of the interposed portion (dimension in a direction orthogonal to the axial direction), the length of the interposed portion (dimension along the axial direction), and the like are also not particularly limited as long as it is possible to achieve the improved joining strength by joining the distal member to a part of the inner layer of the tube body.

The inner layer may not be continuously formed along the axial direction of the tube body. At least, the inner layer is formed to have a length in the axial direction to achieve the joining strength between the tube body and the distal member by being interposed between the outer layer and the distal member.

The anti-kink protector may not be provided in the medical elongated body described in the first embodiment. In addition, the specific application of the medical elongated body is not particularly limited as long as it is possible to use the medical elongated body for a purpose of introducing a medical device (such as a guide wire or various medical instruments for treatment) into a living body.

The balloon catheter described in the embodiment illustrated in FIGS. 5(A)-6(B) may be a so-called over-the-wire type. The balloon catheter may have a guide wire lumen that extends from a distal end to a proximal end of the shaft.

The material constituting each portion of the medical elongated body and the balloon catheter is not particularly limited as long as the material forming the inner layer of the tube body is formed of at least a material having better fusing properties with respect to the material forming the distal member than the fusing properties of the material forming the outer layer of the tube body. It is possible to use a material other than the materials described in the specification. The combination of the materials of each of the constituent members is not limited to the examples discussed above. Appropriate changes can be made. For example, the balloon can be formed of a well-known nylon elastomer or the like.

The detailed description above describes a medical elongated body and a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
   an outer tube shaft comprising a lumen, the outer tube shaft comprising an outer surface and a distal portion;
   an inner tube shaft within the lumen of the outer tube shaft, the inner tube shaft comprising an outer surface and a distal portion;
   an expandable balloon joined to the outer surface of the distal portion of the inner tube shaft and the outer surface of the distal portion of the outer tube shaft,
   the inner tube shaft comprising a tube body and a distal member disposed at a distal end of the tube body, the distal member being more flexible than the tube body, the tube body extending in an axial direction;
   the distal end of the tube body being joined to the distal member at a joint portion;
   the tube body comprising an outer layer and an inner layer disposed inside of the outer layer in the radial direction;
   the inner layer being more compatible for fusing to the distal member than the outer layer; and
   the inner layer being interposed between the distal member and the outer layer by extending radially outwardly between the distal member and the outer layer at the joint portion.

2. The balloon catheter according to claim 1, wherein
   the inner layer of the tube body is a modified polyolefin resin, and
   the distal member is a polyurethane resin.

3. The balloon catheter according to claim 2, wherein each of the outer layer, the outer tube shaft, and the balloon of the tube body is a polyamide resin.

4. The balloon catheter according to claim 3, wherein
   the modified polyolefin resin of the inner layer is directly connected to the polyurethane resin of the distal member, and
   the polyurethane resin of the distal member is not connected with the polyamide resin of the outer layer.

5. The balloon catheter according to claim 1,
   the inner layer is in continuous contact with the outer layer along the axial direction of the tube body, and
   the inner layer material comprises a lower sliding resistance than the outer layer material.

6. A medical elongated body comprising:
   a tubular body comprising a lumen, the tubular body comprising a distal end and extending in an axial direction;
   a distal member joined to the distal end of the tubular body at a joint portion, the distal member being more flexible than the tubular body, the distal member comprising a distal lumen that communicates with the lumen of the tubular body;
   the distal end of the tubular body being joined to the distal member at a joint portion;
   the tubular body comprising an outer layer and an inner layer, the inner layer and the outer layer being made of different material compositions, the inner layer comprising an elongated portion and a distal portion, the elongated portion of the inner layer being radially inside the outer layer, the outer layer comprising an outer surface and an inner surface;
   the inner layer being more compatible for fusion to the distal member than the outer layer; and
   the distal portion of the inner layer extending radially outwardly relative to the inner surface of the outer layer so that the distal portion of the inner layer is positioned between the outer layer and the distal member in the axial direction.

7. The medical body according to claim 6, wherein the distal portion of the inner layer extending radially outwardly prevents the outer layer from contacting the distal member.

8. The medical body according to claim 6, wherein the distal lumen of the distal member is open to the outside environment.

9. The medical body according to claim 6, wherein the distal portion of the inner layer is flared radially outwardly.

10. The medical body according to claim 6, wherein
the inner layer of the tubular body is a modified polyolefin resin, and
the distal member is a polyurethane resin.

11. The medical body according to claim 6, wherein
the elongated portion of the inner layer comprises a radially outer surface and extends continuously in the axial direction along an axial extent, and
the inner surface of the outer layer is fixed to the radially outer surface of the elongated portion of the inner layer along the axial extent.

12. The medical body according to claim 6, wherein
the distal portion of the inner layer comprises a distal-most end, and
the distal-most end of the distal portion of the inner layer comprises an outer diameter equivalent to the outer layer.

13. The medical body according to claim 12, wherein
the distal portion of the inner layer comprises a proximal surface and a distal surface positioned distal to the proximal surface;
the proximal surface of the distal portion of the inner layer is connected to the inner surface of the outer layer; and
the distal surface of the distal portion of the inner layer is fused to the distal member at the joint portion.

14. The medical body according to claim 6, wherein
the inner layer comprises a wall thickness and the outer layer comprises a wall thickness, and
the wall thickness of the inner layer is less than the wall thickness of the outer layer proximal to the joint portion.

\* \* \* \* \*